United States Patent [19]

Horigome et al.

[11] Patent Number: 4,615,769
[45] Date of Patent: Oct. 7, 1986

[54] PROCESS FOR DISTILLATION OF STYRENES

[75] Inventors: Tsukumo Horigome; Noriyuki Kawabe, both of Oita; Mamoru Takiue, Fukuoka; Kunihiko Imai, Iwatsuki; Noriaki Uchiyama, Chofu; Fusayuki Tsuzuki, Nagareyama; Kenji Shimada, Kudamatsu; Masahiro Shibuya, Hachioji; Norimasa Hakutoh, Kashiwa; Chiaki Watanabe; Junichi Abe, both of Ichikawa, all of Japan

[73] Assignees: Nippon Steel Chem. Co., Ltd.; Hitachi, Ltd., both of Tokyo, Japan

[21] Appl. No.: 727,059

[22] Filed: Apr. 25, 1985

[30] Foreign Application Priority Data

Apr. 26, 1984 [JP] Japan .................. 59-082863
Aug. 22, 1984 [JP] Japan .................. 59-174702
Aug. 24, 1984 [JP] Japan .................. 59-176392
Dec. 28, 1984 [JP] Japan .................. 59-278874

[51] Int. Cl.<sup>4</sup> .......................... B01D 3/42; C07C 7/04
[52] U.S. Cl. .......................................... 203/2; 203/3; 203/21; 203/26; 203/94; 203/DIG. 7; 203/DIG. 9; 202/182; 202/206; 585/440; 585/800
[58] Field of Search ............. 585/441, 440, 806, 800; 202/206, 160, 182; 203/26, 23, 21, 3, 2, DIG. 7, 98, 91, 94, DIG. 9

[56] References Cited

U.S. PATENT DOCUMENTS

| | | | |
|---|---|---|---|
| 3,004,089 | 10/1961 | Hutto | 203/3 |
| 3,187,066 | 6/1965 | Nathan | 203/26 |
| 3,256,355 | 6/1966 | Gilman et al. | 585/441 |
| 3,414,484 | 12/1968 | Carson et al. | 203/26 |
| 3,438,870 | 4/1969 | Roscher et al. | 203/60 |
| 3,515,764 | 2/1970 | Hallman et al. | 585/441 |
| 4,056,444 | 11/1977 | Weicht et al. | 203/26 |
| 4,177,137 | 12/1979 | Kruse | 203/26 |
| 4,395,310 | 7/1983 | Idenden | 203/26 |

FOREIGN PATENT DOCUMENTS 308736 5/1930 United Kingdom .................. 203/26

Primary Examiner—Wilbur Bascomb
Attorney, Agent, or Firm—Armstrong, Nikaido, Marmelstein & Kubovcik

[57] ABSTRACT

The present invention provides a process for distillation of styrenes which can be stably operated without loss of energy saving effect, by leading a part or all of low boiling point component vapor from the top to a compressor to use as a heat source for a reboiler and returning the low boiling point components condensed in the reboiler or a mixture of the condensate and a part of the uncondensed vapor to a recycling line of a distillation column.

6 Claims, 1 Drawing Figure

PROCESS FOR DISTILLATION OF STYRENES

BACKGROUND OF THE INVENTION

1. Field of the invention

The present invention relates to a process for distillation of styrenes by a heat pump system.

2. Description of the Prior Art

In distillation, heat is required for vaporizing the liquid and cooling is required for condensing the vaporized vapor. The amount of heat needed for vaporization is approximately the same as released in condensation. Particularly for purpose of improving the efficiency of distillation operation, it is important to decrease the amount of heat required for vaporization. For decreasing the amount of heat used in distillation columns, processes for distillation by a heat pump system are known (U.S. Pat. No. 4,056,444, Published Unexamined Japanese Patent Application No. 111,466/77, Published Examined Japanese Patent Applications No. 39,236/79). These processes for distillation comprise adiabatic compression of the vapor of low boiling point components discharged from the top of a distillation column with a compressor to elevate its temperature and use of latent heat of the vapor as a heat source for the reboiler. In these processes, the vapor from the top of the distillation column can be utilized as a heat source by externally adding a small quantity of energy. For this reason, these processes for distillation are said to be extremely useful from the viewpoint of thermal economy, as compared to ordinary distillation system.

Now, styrenes such as styrene, vinyltoluenes, α-methylstyrene, etc. are prepared by dehydrogenation of the corresponding ethylbenzenes such as ethylbenzene, ethyltoluenes, cumene, etc. These dehydrogenated oils (crude styrenes) are mainly composed of the resulting styrenes and the unreacted ethylbenzenes, which contain small quantities of light components such as benzene, toluene, etc. and heavy components such as styrene oligomers. Accordingly, it is necessary to separate and remove the light components and heavy components from the aforesaid dehydrogenated oils, upon preparation of styrenes. As such a process, a process for distillation using a plurality of distillation columns has been adopted.

However, the boiling points of styrenes are closely akin to those of ethylbenzenes. For example, in the case of styrene and ethylbenzene, the boiling point of the former is 145.2° C. and the latter is 135.2° C., under atmospheric pressure. The difference in boiling point therebetween is merely 9.0° C. Therefore, in order to separate styrenes from ethylbenzenes by distillation, high efficiency of distillation is required and it is thus necessary to increase the number of stages of the distillation columns and the reflux ratio. For this reason, it is common that trays of 60 to 100 stages are set in a distillation column used for distillation of styrenes, in the case of a multi-stage column. It is also common that the reflux ratio is set to a considerably large value of approximately 10. Thus, the difference in pressure between the top and the bottom becomes large from 90 to 250 mmHg. In such a distillation column, therefore, a problem arises in that the energy to be supplied as a heat source becomes too large.

It is desired to adopt the process for distillation by the aforesaid heat pump system as a process for distillation of styrenes. However, when the difference in temperature between the top and the bottom in the distillation column becomes large, it is necessary to increase the compression ratio of the vapor of low boiling point components. Accordingly, it has not been considered to adopt the process for distillation using this heat pump system for distillation of styrenes containing components having close boiling points and also being capable of polymerization.

SUMMARY OF THE INVENTION

An object of the present invention is to provide a process for distillation of styrenes capable of applying a process for distillation by the heat pump system to styrene mixtures obtained during preparation of styrenes and capable of being operated stably.

Another object of the present invention is to provide a process for distillation by a heat pump system in which the response of a distillation column to variation in the composition of feed liquid, variation in heat balance due to change in conditions of the system, etc. is improved so that the distillation column can sufficiently follow the variation in the composition of the feed liquid and which is applicable to distillation of styrenes.

A further object of the present invention is to provide a process for distillation by a heat pump system which is free of problems which tend to occur at the starting up of the distillation in a process for distillation by this heat pump system; for example, a long period of time is required until the distillation system becomes stable, during which the purity of the components obtained by distillation decreases, fouling of equipments or troubles such as plugging up, etc. occur, and trouble with impeller in the compressor occurs, etc.

DETAILED DESCRIPTION OF THE INVENTION

The present invention is directed to a process for distillation of styrenes comprising distilling a mixture of styrenes obtained by dehydrogenation of ethylbenzenes and separating styrenes from ethylbenzenes which comprises feeding said mixture of styrenes into a middle portion of a distillation column of a packed column system operated under a reduced pressure, withdrawing a vapor of low boiling point components mainly composed of ethylbenzenes from the top of said distillation column and withdrawing a liquid of high boiling point components mainly composed of styrenes from the bottom of said distillation column, leading a part or all of said vapor of low boiling point components to its compressor to elevate a temperature by adiabatic compression, then leading the vapor to a reboiler of said distillation column wherein a part or all of said vapor is condensed and the latent heat thereby released is used as a heat source of said reboiler, then returning the condensed low boiling point components or a mixture thereof with a part of the uncondensed vapor to a recycling line of said distillation column and withdrawing the remaining condensed liquid of low boiling components out of the distillation system.

The mixture of styrenes to which the process of the present invention applies is a mixture obtained by dehydrogenating ethylbenzenes and is mainly composed of the resulting styrenes and the unreacted ethylbenzenes, and normally contain small quantities of light components such as benzene, toluene, moisture, air, nitrogen etc., heavy components such as styrene oligomers, polymerization inhibitors etc. The mixtures of styrenes include not only dehydrogenated oils obtained by conventional dehydrogenation reaction with steam but also those obtained by oxidative dehydrogenation in gaseous phase or liquid phase. The above-mentioned styrenes refer to styrene, vinyltoluenes, α-methylstyrene, etc. and ethylbenzenes refer to ethylbenzene, ethyltoluenes, isopropylbenzene, etc.

As modes for formation of distillation columns for distilling the mixture of styrenes, there are, for example, a mode in which light components having boiling points lower than ethylbenzenes are separated in a first column, then ethylbenzenes are separated from styrenes and heavy components having boiling points higher than ethylbenzenes in a second column and styrenes are further separated from the heavy components in a third column; a mode in which in a first column ethylbenzenes and light components having boiling points lower than ethylbenzenes are withdrawn from the top, and from the bottom, styrenes and heavy components having boiling points higher than ehtylbenzenes are separately withdrawn, and then the top distillate and the bottom distillate are fed in a second column, respectively, wherein light components are separated from ethylbenzenes with respect to the above-mentioned top distillate and with respect to the bottom distillate, styrenes are separated from heavy components; etc. The present invention is applicable to any of the modes described above. Preferably, the distillation column to which the present invention is to be applied is the second column in the former case and the first column in the latter case. Accordingly, the mixtures of styrenes to which the present invention is applied may be mixtures obtained immediately after dehydrogenation of ethylbenzenes or mixtures obtained by separating and removing light components such as benzene, toluene, etc. having boiling points lower than ethylbenzenes in advance.

The distillation column to which the present invention is applied is a distillation column of the packed type which is operated under a reduced pressure. As packings to be packed in the distillation column, regular packings are preferred; especially packings having a pressure difference below 1.5 mmHg, preferably below 0.8 mmHg, per theoretical stage, are preferred. By the use of such a distillation column, distillation efficiency becomes excellent and the reflux ratio can be reduced. Accordingly, the pressure difference in the distillation column can be reduced to less than 100 mmHg, preferably less than 70 mmHg. As a result, the bottom temperature can be lowered and the temperature difference between the top and the bottom can be reduced.

In the above-described distillation column, a vapor of low boiling point components mainly composed of ethylbenzenes is withdrawn from the top and at the same time, a liquid of high boiling point components mainly composed of styrenes is withdrawn from the bottom. A part or a of the vapor of low boiling point components described above which was withdrawn from the top of the distillation column is led to a compressor. By adiabatic compression with this compressor, the temperature is elevated and the vapor of low boiling point components, the temperature of which has been thus elevated, is led to a reboiler of the distillation column. In the reboiler, a part or a of the vapor is condensed. By doing so, the vapor is used as a heat source for the reboiler.

The ratio of the vapor of low boiling point components led to the compressor and the ratio of the vapor condensed in the reboiler are determined taking into consideration the composition of styrene mixtures fed in the distillation column, the composition and quantity of vapor of low boiling point components withdrawn from the top of the distillation column, the efficiency of the compressor, the energy added with this compressor, the amount of heat required for the reboiler of the distillation column, etc. With respect to the vapor of low boiling point components distilled out of the top, preferably, a line for directly leading to a condenser is provided, in which at least a part of the vapor is directly introduced into the condenser so as to keep thermal balance without introducing into the compressor, in order to stabilize the distillation system. In the reboiler, the whole of the vapor may be condensed in the case where light components such as benzene, toluene, etc. having boiling points lower than ethylbenzenes are not contained. However, in the case of the light components are present, it is preferred that the uncondensed vapor remains. It is possible to determine the ratio to be condensed by controlling the pressure of the reboiler. When the pressure is increased, a larger ratio of the vapor can be condensed. However, markedly increased pressure results in increase in load on the compressor. The low boiling point components condensed in the reboiler and a part of the uncondensed vapor are returned to a recycle line of the distillation column and the remaining is discharged from the distillation column. It is advantageous that the condensed low boiling point components are used for preheating of the vapor of low boiling point components fed into the compressor since these condensed components are still at high temperatures.

In the process of the present invention, it is preferred that raw materials for distillation or low boiling point components be previously charged in the distillation column upon starting up of distillation and heated with an auxiliary reboiler using an external heat source to start up distillation in a total refluxing state; the vapor of low boiling point components distilled out of the top of the distillation column is preheated by using the bottom liquid as a heat source; a recycling line for recycling the vapor of low boiling point components, a preheater, a compressor and a vapor-liquid separation tank are previously warmed up by the preheated vapor of low boiling point components; then the temperatures and pressures of the respective parts are controlled in a state approximate to stationary operation conditions of the distillation column; and the vapor of low boiling point components distilled out of the top of the distillation column is flown to thereby shift to normal operation.

Materials to be charged in the bottom of the distillation column upon the starting up of distillation may be styrene mixtures to be distilled but are preferably liquids of low boiling point components having boiling points approximate to those of the low boiling point components contained therein. In case that a liquid of low boiling point components is previously charged, the liquid of low boiling point components may be a single component or a mixture of two or more components as far as they are not capable of polymerization and have different boiling points. As the liquid of low boiling point components, low boiling point components contained in styrene mixtures and withdrawn from the top of the distillation column in distillation are preferably used. The low boiling point components in the styrene mixture are mainly composed of ethylbenzenes and preferably contain less than 5 wt% of styrenes.

Upon controlling the distillation column in the process of the present invention, it is desired that the condensation pressure of the reboiler be controlled by continuously analyzing the composition of the styrene mixture fed in the distillation column, subjecting the results of the analysis of the composition and the internal temperature of the distillation column as a key point of the operation to feed forward control operation and automatically controlling the set pressure of the vapor-liquid separation tank mounted at the exit of the reboiler by its output signal.

The location of a thermometer which is provided for detecting the internal temperature of the distillation column is determined depending upon the composition of the styrene mixture and the dynamic characteristics of the distillation column. In addition, the quantity of low boiling point components to be withdrawn or the amount of heat transfer to the reboiler, preferably both of them, can be cascade-controlled to the above-mentioned internal temperature of the distillation column such that the internal temperature of the distillation column is controlled to a set temperature. Control of the amount of heat transfer to the reboiler can be effected by a gauge for detecting the pressure in the vapor-liquid separation tank, which is mounted at the exit of the reboiler, and a control valve provided at a withdrawal line for withdrawing vapor from the vapor-liquid separation tank.

DESCRIPTION OF THE PREFERRED EMBODIMENTS

Figure 1:
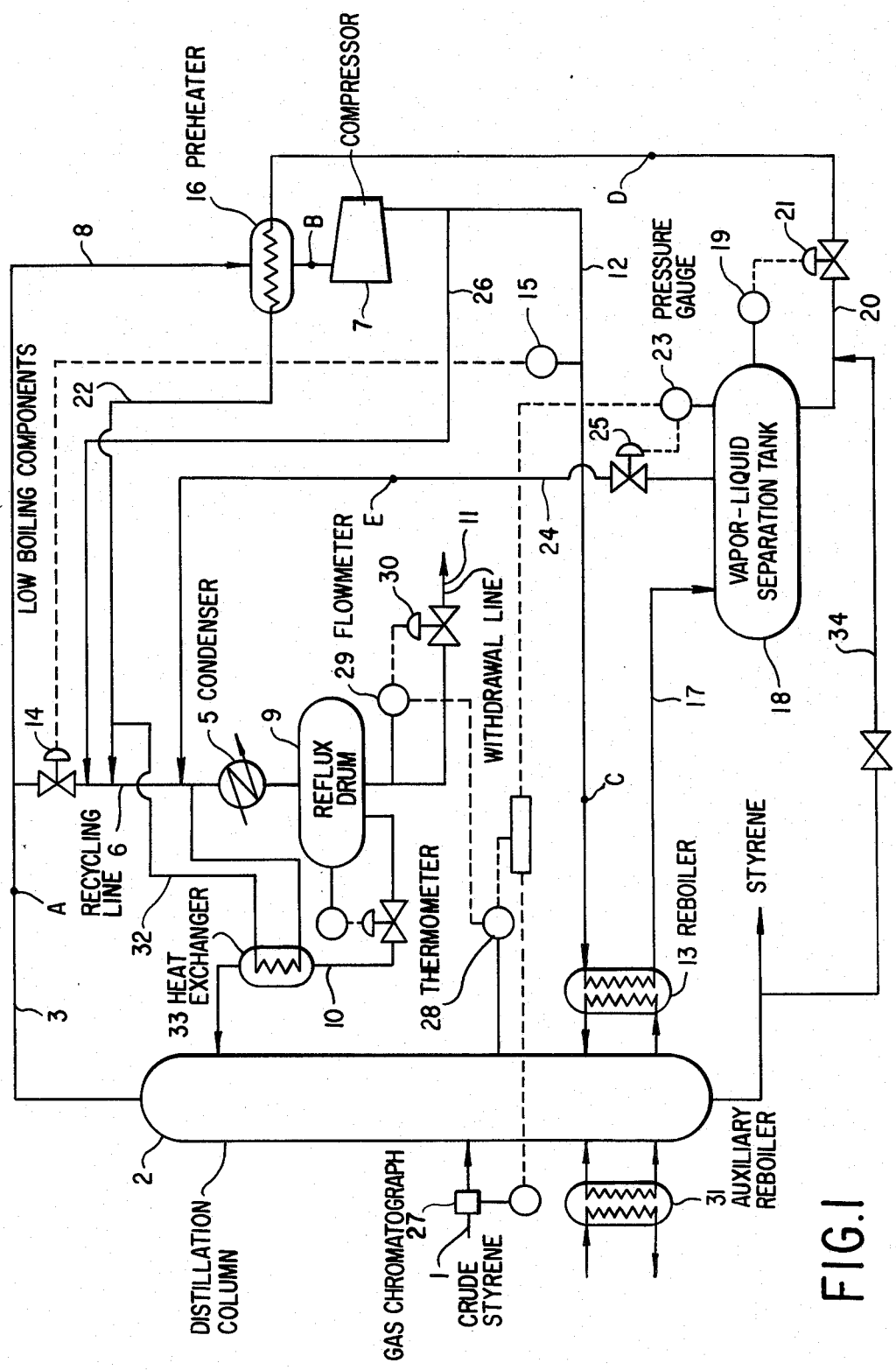
FIG. 1 is a flow sheet showing the process for distillation of styrenes by a heat pump system which is an example in accordance with the present invention.

Referring to the flow sheet shown in the drawing as an example of the present invention applied to a styrene mixture (crude styrene) obtained by dehydrogenation of ethylbenzene, the present invention will be described in detail hereafter.

In FIG. 1, the styrene mixture is fed from feeding line (1) into the middle portion of distillation column (2) of a packed column system which is operated under a reduced pressure. From the top line (3) of the distillation column (2), a vapor of low boiling point components mainly composed of ethylbenzene is withdrawn and, at the same time, a liquid of high boiling point components mainly composed of styrene is withdrawn from line (4) of the bottom.

The vapor of low boiling point components withdrawn from line (3) is divided into line (6) at the side of condenser (5) and line (8) at the side of compressor (7). The vapor of low boiling point components divided into line (6) is condensed with condensor (5) and thereafter once fed into reflux drum (9); a part of the condensed liquid is refluxed from refluxing line (10) to the upper portion of distillation column (2) and the remaining condensed liquid is withdrawn out of the system. Further the vapor of low boiling point components divided into line (8) is adiabatically compressed to elevate to a temperature higher than that of the bottom of the distillation column and then fed from line (12) to reboiler (13), where it is used as its heat source.

Dividing the vapor of low boiling point components into line (6) and line (8) is carried out to mainly control the quantity of the vapor of low boiling point components fed to compressor (7) to a set value and prevent excessive heat supply to the distillation system. The quantity of the vapor divided into line (8) varies depending upon conditions for operation of the distillation system, variations in composition of raw materials, etc. but it is sufficient for the quantity of vapor to be such that the amount of heat added to the reboiler is not excessive, and, the quantity of the vapor divided into line (6) is preferably from 0.5% to 25%. As a method for control of dividing vapor, there can be adopted, for example, a method for control which comprises accumulating the condensate of the vapor of low boiling point components in condenser (5) and controlling the liquid level of the condensate with a liquid level gauge and a control valve at an outlet of the condenser to thereby increase or decrease the surface of heat transfer of the condenser; a method for direct control by providing a control valve at the inlet side of condenser (5) of line (6); etc. In the present flow sheet, control valve (14) is set in line (6) and by opening and shutting the valve in association with flow regulator (15) provided at line (12) at the outlet side of compressor (7), the quantity of the vapor of low boiling point components fed into compressor (7) is maintained at a set value.

Further when the vapor of low boiling point components fed into compressor (7) is saturated vapor, it is condensed either in the compressor or at the outlet line upon adiabatic compression with the compressor; in the compressor, liquid drops cause impeller trouble or polymerization of styrene monomer, by which serious damage is caused in some occasion. It is thus preferred that preheater (16) be provided at the above-mentioned line (8) and the vapor of low boiling point components fed into the compressor be preheated to elevate the temperature.

The vapor of low boiling point components which is fed into compressor (7) and charged in reboiler (13) through line (12) after elevating the temperature with adiabatic compression is used as a heat source. In reboiler (13), a part or all of the low boiling point components is condensed and latent heat mainly generated at this stage is utilized as a heat source. The condensate or the condensate and the vapor of low boiling point components are led into vapor-liquid separation tank (18) via line (17), whereby the condensed low boiling point components are separated from the uncondensed vapor of low boiling point components.

In this case, in order to reduce pressure loss in reboiler (13) and also improve heat transfer efficiency, it is preferred that the line from reboiler (13) to separation tank (18) be divided into a line for leading the condensate into separation tank (18) and a line for leading the uncondensed vapor of low boiling point components into separation tank (18). The components condensed in this reboiler (13) are components having relatively high boiling points among the vapor of low boiling point components and are mainly composed of ethylbenzenes. Further the uncondensed components which pass through reboiler (13) in uncondensed state are components having relatively low boiling points among the vapor of low boiling point components and are mainly composed of benzene, toluene, moisture, air, nitrogen, etc.

In the flow sheet, the condensed low boiling point components withdrawn from the bottom of separation tank (18) are introduced into preheater (16) this flow being controlled by liquid level gauge (19) and control valve (21) provided at line (20). After the condensed components are heat-exchanged in the preheater with the vapor of low boiling point components fed into compressor (7) by this preheater (16), the components are combined with line (6) via line (22). Preferably, the condensate is fed into heat exchanger (33) via line (32) and utilized for maintaining the reflux returned to distillation column (2) at a constant temperature since the condensate is still kept at a high temperature. Further the vapor of low boiling point components withdrawn from the upper portion of separation tank (18) is withdrawn while being controlled with pressure gauge (23) provided on the separation tank and pressure control valve (25) provided in line (24) and combined with line (6) through this line (24). By controlling the vapor of low boiling point components in reboiler (13) so as not to completely condense in such a manner, components having relatively high boiling points in the vapor of low boiling point components can be selectively condensed and the condensation temperature in reboiler (13) becomes high. Further, the heat transfer per unit condensation amount can be increased. In addition, the compression ratio of compressor (7) can be reduced so that running costs can be minimized and the costs for equipments can be reduced. Furthermore, there is an advantage that the temperature of the low boiling point components condensed in this reboiler (13) can be maintained at a temperature necessary for and sufficient for heating the vapor of low boiling point components in preheater (16). Control of the condensation amount of the vapor of low boiling point components in the reboiler can be performed by controlling the pressure of the reboiler, namely, the pressure of separation tank. For example, when the pressure is increased, a larger amount of the vapor is condensed and the heat transfer amount also increases; alternatively, when the pressure is decreased, the heat transfer amount can be reduced or the compression pressure can be reduced.

The variation of the vapor of low boiling point components fed into compressor (7) directly influences the variation of the vapor of low boiling point components fed into reboiler (13). Accordingly, in order to stably operate the distillation system, a control valve (not shown) having good accuracy may be provided at bypass line (26) from compressor (7) to condenser (5) to thereby absorb minute variations of heat capacity incapable of being controlled by compressor (7).

For driving compressor (7), there are various methods such as a motor alone, combination of a motor and a steam turbine, a steam turbine alone, etc. However, it is preferred that a system for accurately controlling rotating speed be provided in a driving machine of compressor (7) in order to achieve stabilization of the distillation system. As the mechanism for controlling the rotating speed, it is possible to adopt a VVVF (variable voltage variable frequency) control system, a VV (variable voltage) control system, etc. For variation of voltage or frequency of an electric source or variation in pressure of steam, a feedback control system is incorporated to control the rotating speed, namely, capacity variation.

In order to stably operate the distillation system, the following control is additionally carried out in this example.

Namely, gas chromatograph (27) which continuously analyzes the composition of components of the styrene mixture fed into distillation column (2) is provided at feeding line (1) and at the middle portion of distillation column (2), thermometer (28) for detecting the internal temperature of the column is provided and, flow meter (29) for detecting the flow amount of the vapor of low boiling point components withdrawn and control valve (30) for controlling the flow amount are provided at withdrawal line (11) from reflux drum (9).

Further, the internal temperature of the column detected with thermometer (28), the withdrawn quantity detected by flow meter (29) and the vapor pressure of separation tank (18) detected by pressure gauge (23) are cascaded-controlled, respectively. At the same time, the results of the analysis of gas chromatograph (27) and the internal temperature of distillation column (2) detected by thermometer (28) are subjected to feed forward control operation, by an output signal from which the set pressure of the vapor of low boiling point components in separation tank (18) is controlled. The equation for the feed forward operation is appropriately determined depending upon the composition of the styrene mixture fed in distillation column (2) through feeding line (1) and the dynamic characteristics of the distillation column.

In this example, in case the composition of the styrene mixture fed from feeding line (1) varies, when the low boiling point components increase, feed forward operation works so as to control the internal temperature of the distillation column to the set value based on the analytical results and the results of measuring the internal temperature of the distillation column; by an output signal from the operation, control valve (30) is controlled so as to increase the amount of the low boiling point components withdrawn and control valve (25) is designed to control so as to increase the pressure in reboiler (13) in order to elevate the condensation temperature of the vapor of low boiling point components and increase the heat transfer amount in reboiler (13). Conversely when the low boiling point components decrease, control is performed in the opposite manner of the case where the above-mentioned low boiling point components increase.

Further in case that reboiler (13) alone is insufficient for the heat source of distillation column (2), or, in order to supply heat necessary for start up, it is desired to provide auxiliary reboiler (31) for introducing external heat source such as steam, etc., in distillation column (2). Upon starting up of distillation, it is designed such that raw materials for distillation or low boiling point components are previously charged in distillation column (2) and heated with the auxiliary reboiler to start up distillation in a total refluxing state; liquid at the bottom of the distillation column is flown through line (34) and fed into preheater (16) via line (20) to preheat the vapor of low boiling point components distilled out of the top; recycling lines (3), (6), (8), (10), (12), (17), (20), (22) and (24), preheater (16), compressor (7), reboiler (13) and separation tank (18) are previously warmed up with the preheated vapor of low boiling point components; then the temperature and pressure at each portion are regulated to conditions closely similar to stationary running conditions of distillation column (2), thereafter raw materials are fed and, the compressed vapor of low boiling point components is flown in reboiler (13) to shift to normal running.

Further in this example, in case of the starting up of the distillation system or in case that the quantity of the vapor of low boiling point components is small in separation tank (18), inert gases such as nitrogen gas, etc. may be introduced into separation tank (18) for smooth control of the condensing pressure.

EXAMPLE 1

Dehydrogenated oil having the composition shown in Table 1, which had been obtained by dehydrogenating ethylbenzene in accordance with the distillation system of the example shown in FIG. 1, was distilled. In the distillation, a distillation column packed with regular packings (made by SULZER BROTHERS LTD., trademark "MELLAPAK") was used and controlled in such a manner that the pressure difference between the top and the bottom became less than 70 mmHg. In running of the distillation column, dehydrogenated oil was constantly fed and, about 40 parts of low boiling point component liquid were withdrawn from line (11) and about 60 parts of high boiling point component liquid from line (4). The flow amount, temperature and pressure of each of points A, B, C, D and E shown in the FIG. 1 were controlled to show the values shown in Table 2. The compositions of the low boiling point components and the liquid withdrawn from the bottom of distillation column (2) are as shown in Table 1.

It has been confirmed that in this example, distillation of styrene can be performed in an extremely stable manner and energy consumption of compressor (7) is about 30% in average of the case where stream alone was employed; resulting in remarkably saving of energy consumption.

TABLE 1

| Component | Dehydrogenated Oil (wt %) | Top Distillate (wt %) | Liquid Withdrawn From the Bottom (wt %) |
| --- | --- | --- | --- |
| Benzene | 0.67 | 1.67 | — |
| Toluene | 2.25 | 5.61 | — |
| Non-aromatic hydrocarbons | 0.16 | 0.34 | 0.04 |
| Ethylbenzene | 34.45 | 90.50 | 0.04 |
| Styrene | 61.88 | 1.86 | 97.61 |
| Heavy components | 0.48 | — | 2.31 |
| Water | 0.11 | — | — |

TABLE 2

| Point | Flow Amount (A = 100) | Temperature (°C.) | Pressure (mm Hg) |
| --- | --- | --- | --- |
| A | 100 | 73 | 105 |
| B | 95 | 83 | 90 |
| C | 95 | 124~126 | 425 |
| D | 90 | 120 | — |
| E | 5 | 120 | 110 |

EXAMPLE 2

Distillation was performed using dehydrogenated oil having the composition shown in Table 3, instead of dehydrogenated oil of the Example 1. The compositions of the low boiling point components and the liquid withdrawn from the bottom of distillation column (2) are as shown in Table 3. The flow amount, temperature and pressure at each of points A, B, C, D and E were controlled to show the values shown in Table 4. The distillation of styrene could be performed also in an extremely stable manner in this Example 2.

TABLE 3

| Component | Dehydrogenated oil (wt %) | Top Distillate (wt %) | Liquid Withdrawn From the Bottom (wt %) |
| --- | --- | --- | --- |
| Benzene | 0.10 | 0.21 | — |
| Toluene | 0.16 | 0.42 | — |
| Non-aromatic hydrocarbons | 0.10 | 0.22 | 0.04 |
| Ethylbenzene | 37.59 | 97.20 | 0.04 |
| Styrene | 61.50 | 2.31 | 97.63 |
| Heavy components | 0.45 | — | 2.30 |
| Water | 0.10 | — | — |

TABLE 4

| Point | Flow Amount (A = 100) | Temperature (°C.) | Pressure (mm Hg) |
| --- | --- | --- | --- |
| A | 100 | 75 | 105 |
| B | 88 | 83 | 90 |
| C | 88 | 125 | 425 |
| D | 86 | 120 | — |
| E | 2 | 120 | 110 |

EXAMPLE 3

Distillation was performed in a manner similar to Example 1 except that dehydrogenated oil was fed from line (1) at a rate of 100 parts/hr, low boiling point component liquid was withdrawn from line (11) at a rate of 36 parts/hr and high boiling point component liquid was withdrawn from line (4) at a rate of 64 parts/hr. The flow amount at point A was 270 parts/hr. The flow amount, temperature and pressure at each of points A, B, C, D and E were controlled to show the values shown in Table 5. The distillation of styrene could be performed also in an extremely stable manner in this Example 3.

TABLE 5

| Point | Flow Amount (A = 100) | Temperature (°C.) | Pressure (mm Hg) |
| --- | --- | --- | --- |
| A | 100 | 70.2 | 95 |
| B | 99.1 | 75.8 | 319 |
| C | 97.3 | 121.3 | 392 |
| D | 93.7 | 91.9 | — |
| E | 3.7 | 91.9 | 385 |

What is claimed is:

1. In a process for distillation of styrenes by distilling a liquid mixture of styrenes obtained by dehydrogenation of ethylbenzenes and separating styrenes from ethylbenzenes, the improvement which comprises feeding said liquid mixture of styrenes into a middle portion of a distillation column of a packed column type which is operated under reduced pressure;

withdrawing from the top of said distillation column a vapor of low boiling components consisting mainly of ethylbenzenes and withdrawing from the bottom of said distillation column a liquid of high boiling components consisting mainly of styrenes;

leading a large part of said vapor of low boiling components to a compressor to elevate the temperature of said vapor by adiabatic compression and leading the remaining part of said vapor of low boiling components to a condenser;

introducing said compressed vapor of low boiling components to a reboiler of said distillation column wherein a part of said compressed vapor of low boiling components is condensed and the latent heat thereby released is used as a heat source for said reboiler;

leading the condensed liquid of low boiling components condensed in said reboiler and the uncondensed vapor of low boiling components uncondensed in said reboiler to a vapor-liquid separation tank and separating said uncondensed vapor from said condensed liquid;

returning said uncondensed vapor of low boiling components separated in said separation tank to said condenser;

introducing said condensed liquid of low boiling components separated in said separation tank into a preheater wherein the condensed liquid of low boiling components undergo heat exchange with the vapor of low boiling components fed into the compressor through the preheater;

thereafter refluxing a part of said condensed liquid of low boiling components condensed in said condenser and said reboiler to the upper portion of said distillation column via a refluxing line thereof; and withdrawing the remaining condensed liquid of low boiling components from the distillation system.

2. A process for distillation of styrenes according to claim 1, wherein said condensed liquid of low boiling components condensed in the reboiler is fed into a heat exchanger which provides heat for maintaining the reflux to said distillation column at a set temperature said heat exchanger being downstream of the preheater heat exchanger.

3. A process for distillation of styrenes according to claim 1, wherein a part of said compressed vapor of low boiling components is returned from said compressor to said condenser via a by-pass line to thereby absorb minute variations of heat capacity incapable of being controlled by said compressor.

4. A process for distillation of styrenes according to claim 1, wherein the composition of the styrene mixture fed into the distillation column is continuously analyzed by gas chromatography;

the analytical results of the composition from the gas chromatography and the internal temperature of the distillation column are subjected to feed forward control operation;

on the basis of the output signal thereby generated, the vapor pressure of low boiling components in the separation tank and the rate of withdrawal of low boiling components from distillation system are cascade-controlled;

the vapor pressure of low boiling components fed into the reboiler is controlled by the results of the cascade-control, thereby controlling the internal temperature of the distillation column.

5. A process for distillation of styrenes according to claim 1, wherein a part of the raw materials for the distillation is previously charged in the distillation column;

said part of raw materials is preheated with the auxiliary reboiler provided in the distillation column for introducing an external heat source;

said part of raw materials is distilled in a total refluxing state;

then, the vapor of low boiling components distilled out of the top of the distillation column is preheated by using the bottom liquid of the distillation column as a heat source;

a recycling line for recycling said vapor of low boiling components, a preheater, a compressor, and a vapor-liquid separation tank are previously warmed up by the preheated vapor of low boiling components;

the temperatures and pressures of respective parts of the distillation system are controlled in a state approximate to stationary operation conditions of the distillation column; and a continuous feed of raw materials is started and the compressed vapor of low boiling components is fed into the reboiler.

6. A process for distillation of styrenes according to claim 1, wherein a quantity of low boiling components is previously charged in the distillation column;

said low boiling components are preheated with the auxiliary reboiler provided in the distillation column for introducing an external heat source;

said low boiling components are distilled in a total refluxing state; then, the vapor of low boiling components distilled out of the top of the distillation column is preheated by using the bottom liquid of the distillation column as a heat source;

a recycling line for recycling said vapor of low boiling components, a preheater, a compressor, and a vapor-liquid separation tank are previously warmed up by the preheated vapor of low boiling components;

the temperatures and pressures of respective parts of the distillation system are controlled in a state approximate to stationary operation conditions of the distillation column; and a continuous feed of raw materials is started and a compressed vapor of low boiling components is fed into the reboiler.

* * * * *